(12) United States Patent
Li

(10) Patent No.: US 7,001,377 B1
(45) Date of Patent: Feb. 21, 2006

(54) OPTICAL TRACKING SYSTEM AND ASSOCIATED METHODS

(75) Inventor: Haizhang Li, Orlando, FL (US)

(73) Assignee: Alcon RefractiveHorizons, Inc., Dallas, TX (US)

(*) Notice: Subject to any disclaimer, the term of this patent is extended or adjusted under 35 U.S.C. 154(b) by 0 days.

(21) Appl. No.: 10/743,558

(22) Filed: Dec. 22, 2003

(51) Int. Cl.
A61F 9/007 (2006.01)

(52) U.S. Cl. .............................. 606/5; 128/898; 606/4

(58) Field of Classification Search ................ 128/898; 606/4–6
See application file for complete search history.

(56) References Cited

U.S. PATENT DOCUMENTS

| | | | |
|---|---|---|---|
| 5,108,412 A * | 4/1992 | Krumeich et al. ............. | 606/4 |
| 5,422,690 A | 6/1995 | Rothberg et al. | |
| 5,586,980 A * | 12/1996 | Kremer et al. ................. | 606/4 |
| 5,632,742 A | 5/1997 | Frey et al. | |
| 5,752,950 A | 5/1998 | Frey et al. | |
| 5,865,832 A | 2/1999 | Knopp et al. | |
| 5,966,197 A | 10/1999 | Yee | |
| 5,980,513 A | 11/1999 | Frey et al. | |
| 6,179,422 B1 | 1/2001 | Lai | |
| 6,210,401 B1 * | 4/2001 | Lai ............................. | 606/12 |
| 6,280,436 B1 | 8/2001 | Freeman et al. | |
| 6,299,307 B1 | 10/2001 | Oltean et al. | |
| 6,302,879 B1 | 10/2001 | Frey et al. | |
| 6,315,773 B1 | 11/2001 | Frey et al. | |
| 6,367,931 B1 | 4/2002 | Lai | |
| 6,451,008 B1 | 9/2002 | Frey et al. | |
| 6,491,687 B1 * | 12/2002 | Sumiya et al. ................. | 606/5 |
| 6,497,700 B1 * | 12/2002 | LaHaye ......................... | 606/4 |
| 6,568,808 B1 | 5/2003 | Campin | |
| 6,706,036 B1 * | 3/2004 | Lai ............................. | 606/12 |
| 6,786,899 B1 * | 9/2004 | Lai ............................. | 606/4 |
| 2003/0225398 A1 | 12/2003 | Zepkin et al. | |
| 2004/0054359 A1 * | 3/2004 | Ruiz et al. ...................... | 606/5 |
| 2004/0199150 A1 * | 10/2004 | Lai ............................. | 606/5 |

* cited by examiner

Primary Examiner—Henry M Johnson, III
(74) Attorney, Agent, or Firm—Allen, Dyer, Doppelt, Milbrath & Gilchrist, P.A.

(57) ABSTRACT

An eye-tracking method includes the step of removably affixing a ring member to an eye in surrounding relation to a cornea of the eye. A plurality of incident light spots are transmitted onto the ring member, and reflections are detected from the ring member of the incident light spots. By analyzing the reflections, eye movement can be determined. A system for tracking eye movement includes a ring member and a device for removably affixing the ring member to an eye in surrounding relation to a cornea of the eye, such as, for example, by applying a vacuum to the ring. A light transmitter transmits a plurality of incident light spots onto the ring member, and a detector for detecting reflections from the ring member of the incident light spots. A processor and software installed thereon are adapted to perform calculations to determine eye movement from an analysis of the reflections.

16 Claims, 3 Drawing Sheets

OPTICAL TRACKING SYSTEM AND ASSOCIATED METHODS

FIELD OF THE INVENTION

The invention relates generally to optical tracking systems, and more particularly to optical systems used with a corneal ablation device.

BACKGROUND OF THE INVENTION

The use of lasers to erode all or a portion of a workpiece's surface is known in the art. In the field of ophthalmic medicine, modification of corneal curvature is known to be accomplished using ultraviolet or infrared lasers. The procedure has been referred to as "corneal sculpting."

In such a procedure, application of the treatment laser during unwanted eye movement can degrade the refractive outcome of the surgery. The eye movement or eye positioning is critical since the treatment laser is centered on the patient's theoretical visual axis which, practically speaking, is approximately the center of the patient's pupil. However, this visual axis is difficult to determine due in part to residual eye movement and involuntary eye movement known as saccadic eye movement.

Video-based eye tracking systems automatically recognize and track the position of the eye based upon landmarks present within an image of a human eye. Video-based systems, however, have neither sufficient speed nor accuracy to detect high-speed movement.

Previous disclosure of eye tracking systems and methods has been made in U.S. Pat. Nos. 5,980,513; 6,315,773; and 6,451,008, which are co-owned with the present application, and which are hereby incorporated by reference hereinto. In these patents, an eye treatment laser beam delivery and eye tracking system is provided (FIG. 1). A treatment laser and its projection optics generate laser light along an original beam path (i.e., the optical axis of the system) at an energy level suitable for treating the eye. An optical translator shifts the original beam path in accordance with a specific scanning pattern so that the original beam is shifted onto a resulting beam path that is parallel to the original beam path. An optical angle adjuster changes the resulting beam path's angle relative to the original beam path such that the laser light is incident on the eye.

An eye movement sensor detects measurable amounts of movement of the eye relative to the system's optical axis and then generates error control signals indicative of the movement. The parallel relationship between the eye movement sensor's delivery light path and the treatment laser's resulting beam path is maintained by the optical angle adjuster. In this way, the treatment laser light and the eye movement sensor's light energy are incident on the eye in their parallel relationship.

A portion of the eye movement sensor's light energy is reflected from the eye as reflected energy traveling on a reflected light path back through the optical angle adjuster. The optical receiving arrangement detects the reflected energy and generates the error control signals based on the reflected energy. The optical angle adjuster is responsive to the error control signals to change the treatment laser's resulting beam path and the eye movement sensor's delivery light path in correspondence with one another. In this way, the beam originating from the treatment laser and the light energy originating from the eye movement sensor track along with the eye's movement.

The laser beam delivery and eye tracking system 10 includes treatment laser source 11, projection optics 12, X-Y translation mirror optics 13, beam translation controller 14, dichroic beamsplitter 15, and beam angle adjustment mirror optics 16.

After exiting the projection optics 12, beam 17 impinges on X-Y translation mirror optics 13, where beam 17 is translated or shifted independently along each of two orthogonal translation axes as governed by beam translation controller 14.

The eye tracking portion of system 10 includes eye movement sensor 18, dichroic beamsplitter 15, and beam angle adjustment mirror optics 16. The sensor 18 determines the amount of eye movement and uses same to adjust mirrors 19 and 20 to track along with such eye movement. To do this, sensor 18 first transmits light energy 21, which has been selected to transmit through dichroic beamsplitter 15. At the same time, after undergoing beam translation in accordance with the particular treatment procedure, beam 17 impinges on dichroic beamsplitter 15, which has been selected to reflect beam 17 to the beam angle adjustment mirror optics 16.

Light energy 21 and beam 17 preferably retain their parallel relationship when they are incident on an eye 23. Beam angle adjustment mirror optics 16 consists of independently rotating mirrors 19 and 20 under servo control.

Light energy reflected from the eye 23 travels back through optics 16 and beamsplitter 15 for detection at sensor 18. Sensor 18 determines the amount of eye movement based on the changes in reflection energy 22. Error control signals indicative of the amount of eye movement are fed back by sensor 18 to beam angle adjustment mirror optics 16. The error control signals govern the movement or realignment of mirrors 19 and 20 in an effort to drive the error control signals to zero. In doing this, light energy 21 and beam 17 are moved in correspondence with eye movement while the actual position of beam 17 relative to the center of the pupil is controlled by X-Y translation mirror optics 13.

The light energy should preferably lie outside the visible spectrum so as not to interfere or obstruct a surgeon's view of eye 23, and must be "eye safe" as defined by the American National Standards Institute (ANSI), for example, light energy 21 may be infrared light energy in the 900-nanometer wavelength region.

Sensor 18 may be broken down into a delivery portion and a receiving portion (FIG. 2). Essentially, the delivery portion projects light energy 21 in the form of light spots 24–27 onto a boundary (e.g., iris/pupil boundary 28) on the surface of eye 23. The receiving portion monitors light energy 22 in the form of reflections caused by light spots 24–27.

In use, spots 24 and 26 are focused and positioned on axis 29, while spots 25 and 27 are focused and positioned on axis 30 as shown. Axes 29,30 are orthogonal to one another. Spots 24–27 are focused to be incident on and evenly spaced about iris/pupil boundary 28. The four spots 24–27 are of substantially equal energy and are spaced substantially evenly about and on iris/pupil boundary 28. This placement provides for two-axis motion sensing as described in the above-referenced co-owned patents.

This tracking system 10 is effective for eyes dilated to greater than approximately 5.5 mm. It would be desirable to be able to track undilated eyes and those that, even dilated, are less than 5.5 mm, or that have an irregular shape.

SUMMARY OF THE INVENTION

The present invention is useful for sensing eye position and movement by tracking the position of the eye during surgical procedures, such as, for example, photorefractive keratectomy (PRK), phototherapeutic keratectomy (PTK), and laser in situ keratomileusis (LASIK).

A method of the present invention includes the step of removably affixing a ring member to an eye in surrounding relation to a cornea of the eye. A plurality of incident light spots are transmitted onto the ring member, and reflections are detected from the ring member of the incident light spots. By analyzing the reflections, eye movement can be determined.

A system for tracking eye movement comprises a ring member and means for removably affixing the ring member to an eye in surrounding relation to a cornea of the eye, such as, for example, by applying a vacuum to the ring. Means for transmitting a plurality of incident light spots onto the ring member is provided, as well as means for detecting reflections from the ring member of the incident light spots. Calculational means are also provided for determining eye movement from an analysis of the reflections.

This technique may be used on objects other than corneas.

DETAILED DESCRIPTION OF THE PREFERRED EMBODIMENTS

Figure 3:
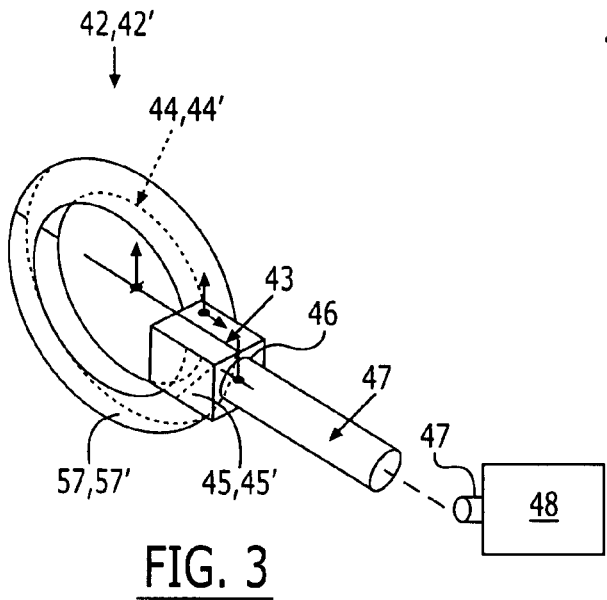
FIG. 3 is a side-top perspective view of a vacuum ring connected to a hose.
Figure 4A:
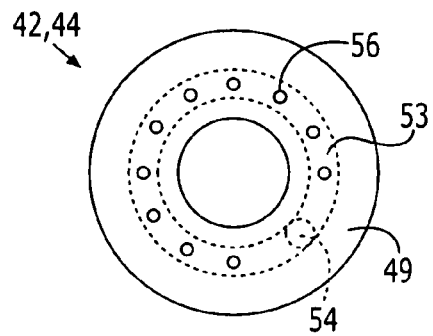
FIGS. 4A and 4B illustrate two embodiments of the inner face of the ring member.
Figure 4B:
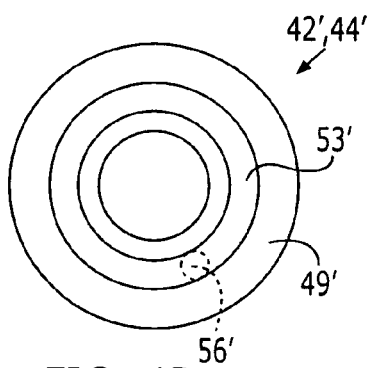

The present invention will now be described with reference to FIGS. 3–5. A system and method for tracking eye movement comprises a tracking device. The tracking device (FIGS. 3–4B) comprises a ring member 42,42'. Two embodiments are presented herein, although these are not intended to limit the invention. Both ring members 42,42' comprise a base 43 affixed to a substantially toroidal ring 44,44'. The base 43 has a channel 45,45' therethrough extending from a hose aperture 46 at an outside of the base 43.

Affixable to the base 43 via the hose aperture 46 is a hose 47. The hose 47 is in fluid communication with a vacuum source 48. An inner face 49,49' of the ring 44,44' is affixable around a cornea 50 and is retainable in place by means of the vacuum source 48 through the hose 47. Preferably a center 51,51' of the ring 44,44' is affixable to be substantially coincident with a center 52 of the cornea 50.

In a first embodiment, the ring member 42 (FIG. 4A) comprises a ring 44 that has a toroidal tunnel 53 and a hole 54 from an outside to the tunnel 53, which is in fluid communication with the base's hose aperture 46 through the channel 45. A plurality of apertures 56 extend between the tunnel 53 and the inner face 49 of the ring 44. Vacuum pressure reaches the cornea 50 from the hose 47 through the base channel 45 to the tunnel 53 and thence to the apertures 56.

In a second embodiment, the ring member 42' (FIG. 4B) comprises a ring 44' that has a substantially toroidal groove 53' in its inner face 49'. The groove 53' is substantially concentric with the ring 44'. A hole 56' extends from an outside of the ring 44' to the groove 53'. The groove 53' is in fluid communication with the base's hose aperture 46 through the channel 45'. Vacuum pressure reaches the cornea 50 from the hose 47 through the base channel 45' to the groove 53' and thence to the hole 56'.

Figure 5:
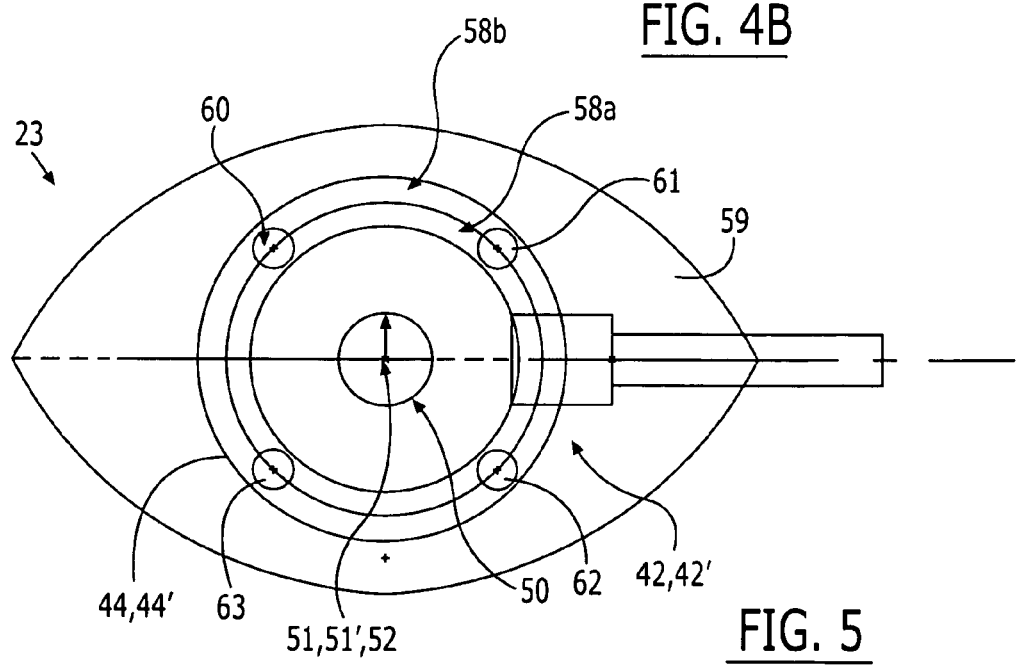
FIG. 5 is a front view of an eye having the vacuum ring attached thereto with light spots transmitted thereon.

Each ring 44,44' preferably comprises a color on its outer face 57,57' that is contrastive with an area of the eye 23 adjacent a location at which the ring member 42,42' is placed, for improving visibility (FIG. 5). For example, the ring's outer face 57,57' may comprise an inner ring 58a that has a light color, such as white, for contrast with the cornea 50; an outer ring 58b having a dark color, such as black, provides contrast with the iris 59.

Figure 1:
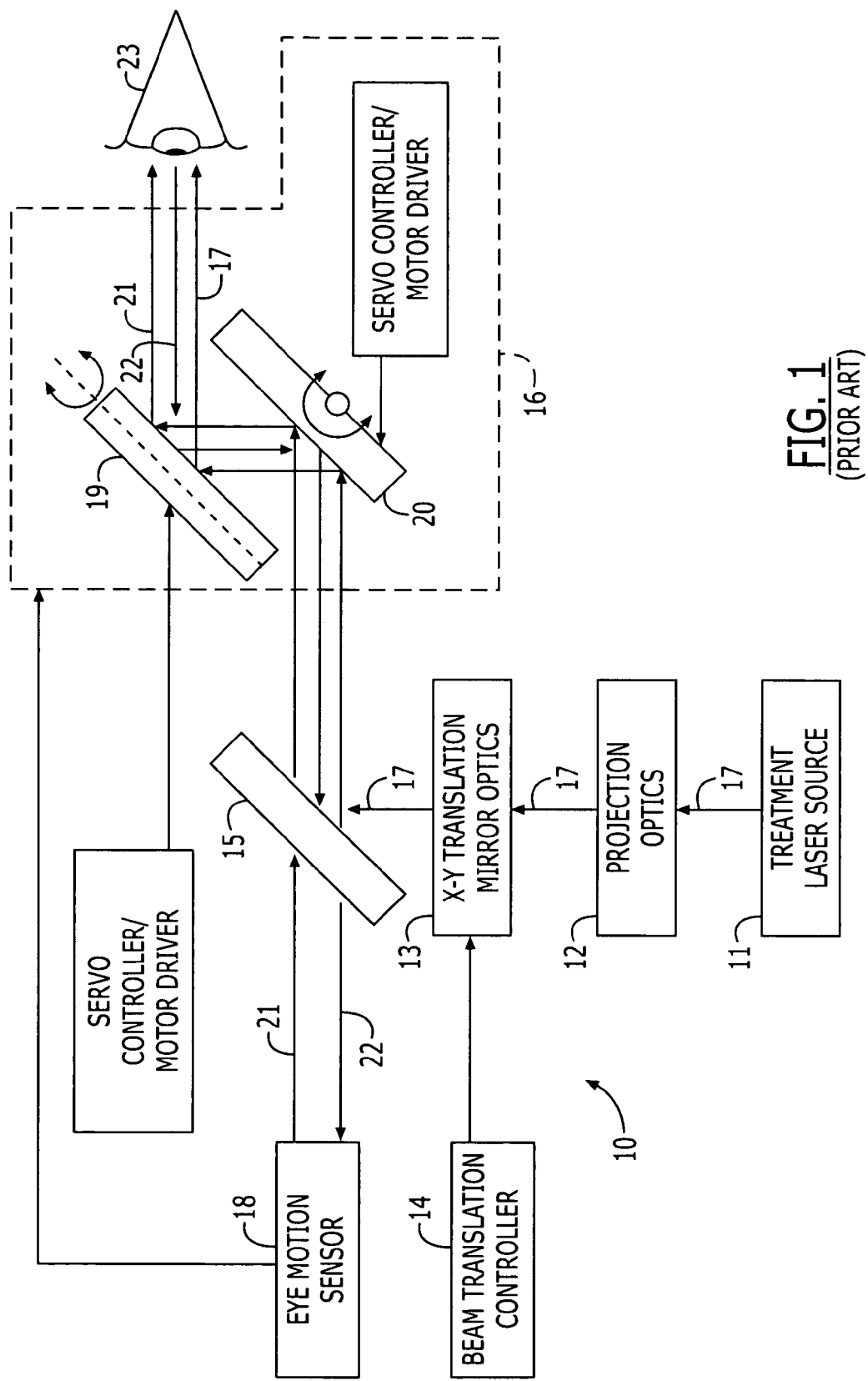
FIG. 1 (prior art) is a block diagram of a laser beam delivery and eye tracking system.
Figure 2:
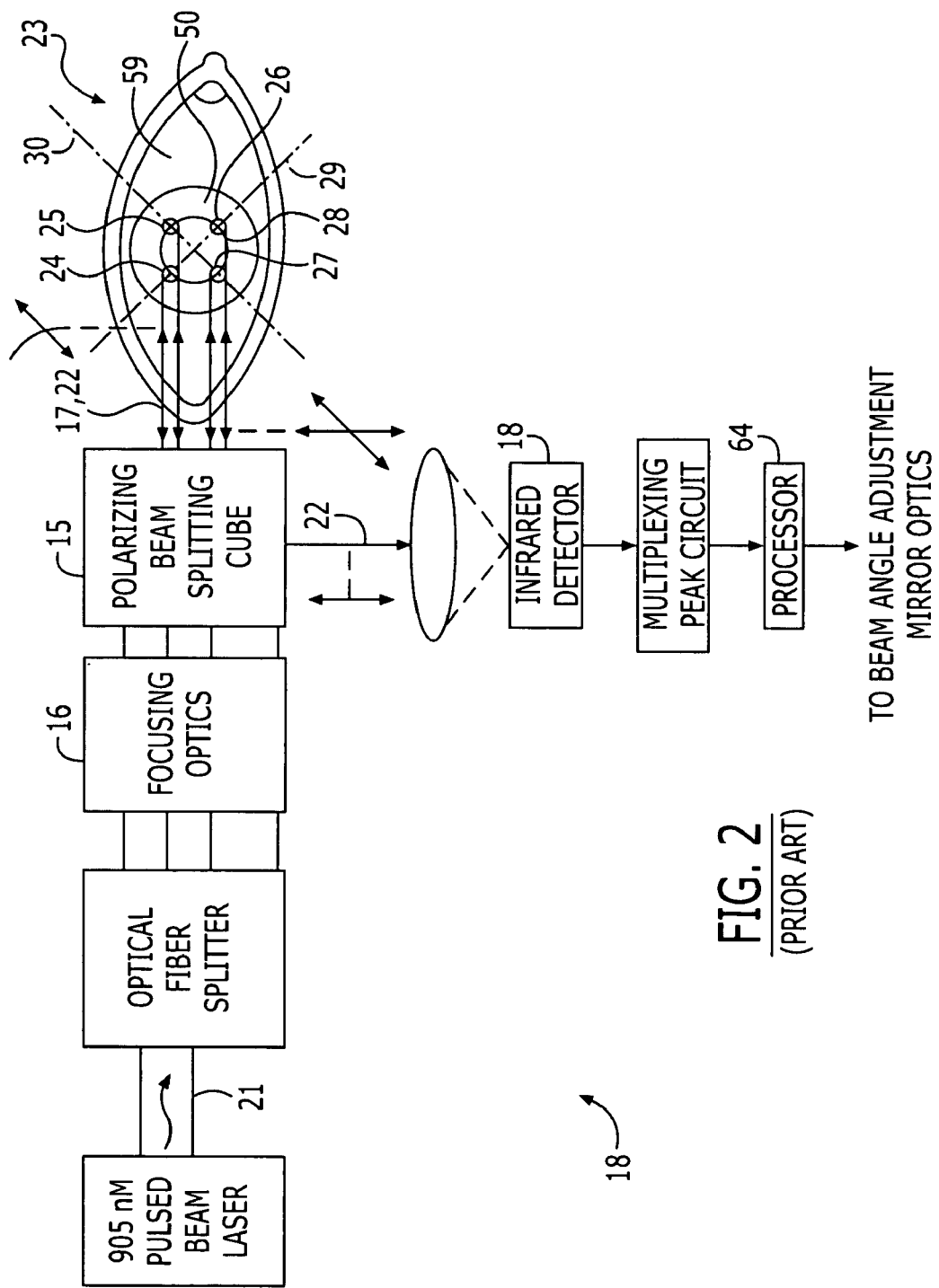
FIG. 2 (prior art) is a block diagram of a prior art eye movement sensor.

Tracking using the ring member 42,42' of the present invention may be achieved in substantially like fashion to that disclosed in the above-referenced '773 patent (FIGS. 1 and 2), wherein a plurality of incident light spots 60–63 are used substantially as the light spots 24–27 of the prior disclosed system 10. The light spots are transmitted 17 from a light source 64 (FIGS. 2 and 5). Reflections 22 of the light spots 60–63 are detected 18, and data from these reflections 22 are used to determine and compensate for eye movement using software resident on a processor 64 in signal communication with the detector 18.

The advantages of the present invention are numerous. Eye movement is measured quantitatively and used to automatically redirect both the laser delivery and eye tracking portions of the system independent of the laser positioning mechanism. The system operates without interfering with the particular treatment laser or the surgeon performing the eye treatment procedure.

Although the invention has been described relative to specific embodiments thereof, there are numerous variations and modifications that will be readily apparent to those skilled in the art in the light of the above teachings. It is therefore to be understood that, within the scope of the appended claims, the invention may be practiced other than as specifically described.

What is claimed is:

1. A method for tracking eye movement comprising the steps of:
    removably affixing a ring member to an eye in surrounding relation to a cornea of the eye, the ring member comprising a color contrastive with an area of the eye adjacent a ring member placement location, the color comprising a light color on an inner ring and a dark color on an outer ring, the inner and the outer rings concentric;
    transmitting a plurality of incident light spots onto the ring member;
    detecting reflections from the ring member of the incident light spots;
    determining eye movement from an analysis of the reflections.

2. The method recited in claim 1, wherein the affixing step comprises applying a vacuum to at least a portion of the ring member along an interface between the ring member and the eye.

3. The method recited in claim 1, wherein the transmitting step comprises transmitting four light spots spaced substantially evenly about the ring member.

4. The method recited in claim 1, wherein the inner ring is white and the outer ring is black.

5. The method recited in claim 1, wherein a center of the ring member is substantially coincident with a center of the cornea.

6. The method recited in claim 1, wherein the ring member comprises:
- a substantially toroidal ring having a toroidal tunnel and a hole from an outside to the tunnel;
- a plurality of apertures extending between the tunnel and an inner face of the ring;
- a base affixed to the ring, the base having a channel therethrough extending from a hose aperture at an outside of the base to the hole; and
- wherein the affixing step comprises placing the ring inner face around the cornea, connecting a hose to the hose aperture, the hose in fluid communication with a vacuum source, and activating the vacuum source.

7. The method recited in claim 1, wherein the ring member comprises:
- a substantially toroidal ring having a substantially toroidal groove in an inner face thereof, the groove substantially concentric with the ring, and a hole from an outside to the groove;
- a base affixed to the ring, the base having a channel therethrough extending from a hose aperture at an outside of the base to the hole; and
- wherein the affixing step comprises placing the ring inner face around the cornea, connecting a hose to the hose aperture, the hose in fluid communication with a vacuum source, and activating the vacuum source.

8. A system for tracking eye movement comprising:
- a ring member comprising a color contrastive with an area of the eye adjacent a ring member placement location, the color comprising a light color on an inner ring and a dark color on an outer ring, the inner and the outer rings concentric;
- means for removably affixing the ring member to an eye in surrounding relation to a cornea of the eye;
- means for transmitting a plurality of incident light spots onto the ring member;
- means for detecting reflections from the ring member of the incident light spots;
- means for determining eye movement from an analysis of the reflections.

9. The system recited in claim 8, wherein the affixing means comprises a vacuum source in fluid communication with at least a portion of the ring member along an interface area for interfacing with the eye.

10. The system recited in claim 9, wherein the vacuum source comprises a hose having a first end in fluid communication with a depression in an inner face of the ring member.

11. The system recited in claim 10, wherein the depression comprises a substantially toroidal groove concentric with the ring member.

12. The system recited in claim 8, wherein the transmitting means comprises means for transmitting four light spots spaced substantially evenly about the ring member.

13. The system recited in claim 8, wherein the inner ring is white and the outer ring is black.

14. The system recited in claim 8, wherein a center of the ring member is affixable to be substantially coincident with a center of the cornea.

15. The system recited in claim 8, wherein the ring member comprises:
- a substantially toroidal ring having a toroidal tunnel and a hole from an outside to the tunnel;
- a plurality of apertures extending between the tunnel and an inner face of the ring;
- a base affixed to the ring, the base having a channel therethrough extending from a hose aperture at an outside of the base to the hole; and
- wherein the affixing means comprises a hose connected to the hose aperture, the hose in fluid communication with a vacuum source, the ring inner face affixable around the cornea and retainable in place by means of a vacuum applied to the ring apertures in contact with the eye.

16. The system recited in claim 8, wherein the ring member comprises:
- a substantially toroidal ring having a substantially toroidal groove in an inner face thereof, the groove substantially concentric with the ring, and a hole from an outside to the groove;
- a base affixed to the ring, the base having a channel therethrough extending from a hose aperture at an outside of the base to the hole; and
- wherein the affixing means comprises a hose connected to the hose aperture, the hose in fluid communication with a vacuum source, the ring inner face affixable around the cornea and retainable in place by means of a vacuum applied to the ring apertures in contact with the eye.

* * * * *